United States Patent
Baid et al.

(10) Patent No.: US 11,331,427 B2
(45) Date of Patent: May 17, 2022

(54) INTRAVENOUS INFUSION SET

(71) Applicant: POLY MEDICURE LIMITED, Faridabad (IN)

(72) Inventors: Rishi Baid, New Dehli (IN); Vipul Chopra, Faridabad (IN)

(73) Assignee: POLY MEDICURE LIMITED, Faridabad (IN)

( * ) Notice: Subject to any disclaimer, the term of this patent is extended or adjusted under 35 U.S.C. 154(b) by 190 days.

(21) Appl. No.: 15/767,593

(22) PCT Filed: Sep. 22, 2017

(86) PCT No.: PCT/IB2017/055763
§ 371 (c)(1),
(2) Date: Apr. 11, 2018

(87) PCT Pub. No.: WO2017/191622
PCT Pub. Date: Nov. 9, 2017

(65) Prior Publication Data
US 2018/0304009 A1    Oct. 25, 2018

(30) Foreign Application Priority Data

Nov. 10, 2016   (IN) .............................. 201611038453

(51) Int. Cl.
*A61M 5/168*     (2006.01)
*A61M 5/14*      (2006.01)
(Continued)

(52) U.S. Cl.
CPC ...... *A61M 5/16822* (2013.01); *A61M 5/1411* (2013.01); *A61M 5/162* (2013.01);
(Continued)

(58) Field of Classification Search
CPC ...................... A61M 5/16822; A61M 5/1411; A61M 5/162; A61M 5/165; A61M 5/36; A61M 5/38; A61M 2005/1657
See application file for complete search history.

(56) References Cited

U.S. PATENT DOCUMENTS 3,882,026 A * 5/1975 McPhee ................ A61M 5/165
                                              210/446
6,814,433 B2 * 11/2004 Putman ................ B41J 2/17513
                                              347/86
(Continued)

FOREIGN PATENT DOCUMENTS

| CN | 202409663 U | 9/2012 |
| CN | 203898866 U | 10/2014 |
| CN | 203898866 U * | 10/2014 |

OTHER PUBLICATIONS

Ding, et al. CN203898866U. Oct. 29, 2014. Machine Translation of Description. Retrieved from https://worldwide.espacenet.com/patent/search?q=cn203898866 on Feb. 19, 2020. (Year: 2014).*

(Continued)

*Primary Examiner* — Nathan R Price
*Assistant Examiner* — Melissa A Snyder
(74) *Attorney, Agent, or Firm* — Moore & Van Allen PLLC; Henry B Ward, III

(57) ABSTRACT

The present invention relates to an intravenous infusion set providing delivery of intravenous fluid to patients. An intravenous infusion set (10) to administer continuous air free delivery of intravenous fluid to a patient, said intravenous infusion set (10) comprising: a drip chamber (12), a flexible infusion line (22) of sufficient length connecting a lower end (20) of the drip chamber (12) to a standard connector (24) at the patient end so that a needle or a catheter could be connected to the patient; a roller clamp (26) arranged between the drip chamber (12) and the standard connector (Continued)

(24) being movable along the length of the flexible infusion line (22), said drip chamber (12) provided with a spike (14) on the upper end (16) and a flow regulating and stopping member (18) at its lower end (20) configured to administer continuous air free delivery of intravenous fluid to patients.

13 Claims, 5 Drawing Sheets

(51) Int. Cl.
| | |
|---|---|
| *A61M 39/28* | (2006.01) |
| *A61M 5/165* | (2006.01) |
| *A61M 5/162* | (2006.01) |
| *A61M 5/36* | (2006.01) |
| *A61M 5/38* | (2006.01) |
| *A61M 39/10* | (2006.01) |

(52) U.S. Cl.
CPC .............. *A61M 5/165* (2013.01); *A61M 5/36* (2013.01); *A61M 5/38* (2013.01); *A61M 39/285* (2013.01); *A61M 39/10* (2013.01); *A61M 39/28* (2013.01)

(56) References Cited

U.S. PATENT DOCUMENTS

| | | |
|---|---|---|
| 2011/0275988 A1 | 11/2011 | Davis et al. |
| 2015/0018765 A1* | 1/2015 | Wong ...................... A61M 5/38 604/126 |
| 2017/0165435 A1* | 6/2017 | Green ..................... A61M 5/14 |
| 2019/0030486 A1* | 1/2019 | Leuthold ................ B01D 61/16 |

OTHER PUBLICATIONS

International Search Report and Written Opinion for International Patent Application No. PCT/IB2017/055763 dated Jan. 31, 2018.

* cited by examiner

INTRAVENOUS INFUSION SET

FIELD OF THE INVENTION

The present invention relates to an intravenous infusion set providing delivery of intravenous fluid to patients. More particularly, the invention relates to an intravenous infusion set with a drip chamber having a flow regulating and stopping member to administer continuous air free delivery of intravenous fluid to patients under gravitational pull. In particularly, the invention relates to an intravenous infusion set with auto-stop function. The flow regulating and stopping member is configured to allow the delivery of continuous air free intravenous fluid till the time it does not come into contact with air. As such, said member is configured to prevent air or any foreign matter from entering the flexible infusion line through the drip chamber. The flow regulating and stopping member is a hydrophilic membrane which is permeable to fluid and impermeable to air which prevents air embolism in patients especially when the drip chamber is empty.

BACKGROUND OF THE INVENTION

Intravenous infusion sets with a drip chamber having flow regulating and stopping members are already known and used to administer controlled quantities of intravenous fluid (for example glucose solution, saline solution, medicine, blood, blood components, etc.) into a patient's body seeking treatment. Such infusion sets are either pump driven or gravity driven infusion devices.

Gravity driven infusion devices typically include a drip chamber with or without a flow regulating and stopping member, a length of flexible infusion line to connect the lower end of the drip chamber to a standard connector. The connector is then connected via conventional access means such as a needle, a catheter or the like to a patient. The upper end of the drip chamber is provided with a spike which is used to pierce a fluid source, such as a bag or bottle containing a specified infusion fluid.

Generally, the whole assembly comprising the fluid source, the spike and the drip chamber is hung on a hanger to provide sufficient height so that the infusion fluid is driven by gravitational force allowing the infusion fluid to flow downward towards the patient from the fluid source. A standard fluid flow adjustment device, for example a roller clamp, is provided on the flexible infusion line between the drip chamber and the connector for regulating the rate of flow of the infusion fluid. The roller clamp can be used to stop the flow of fluid through the flexible infusion line as soon as the fluid source containing the fluid is near to being empty or is empty.

However, various problems and disadvantages are associated with such infusion devices comprising a drip chamber with or without a flow regulating and stopping member. One of the major problems commonly faced is that a certain amount of air in the form of bubbles may get into the blood circulation of the patient accidentally during the infusion procedure, which may lead to air embolism. The air embolism in a patient may cause breathlessness, chest pain, stroke, wheezing, fast heartbeat, loss of consciousness or the like, and may lead to death.

The air embolism in such infusion devices may be caused by fast dripping of the intravenous fluid or due to improper priming of the flexible infusion line at the start of the infusion procedure or when the fluid source runs empty and the infusion process is not stopped or when the infusion set is placed improperly or at a slant position during an emergency, or in the like instances. In such instances, continuous monitoring by a medical practitioner or an attendant becomes necessary to check presence of air bubbles in the flexible infusion line and manually push the air bubbles out of the infusion line, if found. This manual watch takes up much of the medical staff time and may be crucial in a medical condition. In a case, where re-priming is needed, it also may increase the chances of a catheter infection. Moreover, improper priming may lead to an ineffective working of the intravenous infusion sets and can be crucial in critical medical conditions.

To prevent air from entering the infusion tubing, various methods have been used. One of the methods used is by incorporating an air stop membrane into the infusion set, for example by a disk using different processes such as ultrasonic welding, heat sealing, press fit, snap fit, laser welding, clamping by any source or the like to achieve auto-stop function once the drip chamber is empty. However, in a commercially available infusion set with air stop membrane, an improper priming of the infusion line will still result in air bubbles being sucked into the infusion line due to a deformation caused during priming between the air stop membrane and the drip chamber, creating a hair line space and passages. Air bubbles being sucked into the infusion line is also possible due to the roller clamp adjustment during a setup and during a changing of a new infusion bottle. It has been found that the air got trapped from the periphery of the disc, containing the air stop membrane, and entering down in the fluid path, causing air bubbles in the infusion tubing.

The design of the roller clamp could also cause air embolism when it is used alone in an infusion device with an air stop membrane. The roller clamp works on the principle that the infusion line is gradually pressed by the roller clamp to the correct amount of compression to provide the required flow rate. Because the roller clamp presses and moves along the surface of the infusion line in both directions during adjustment and locking, extra positive or negative pressures will be generated in the liquid which will ultimately act on the lower surface of the membrane. The amount of this extra pressure generated would depend on the speed that the roller clamp is moved. Occasionally it could create a suction pressure which is larger than the bubble pressure point of the wetted membrane and air bubbles would be sucked through the membrane into the infusion line.

Relevant prior art is disclosed in CN 203898866 U.

Accordingly, it is desired to provide an improved intravenous infusion set having a drip chamber with a flow regulating and stopping member to administer continuous air free delivery of intravenous fluid to patients, which overcomes the above-discussed disadvantages and is inexpensive to manufacture, efficient, effective and simple in its construction and use.

To overcome the problems described above, the inventors of the present invention have found that air bubbles can be prevented from entering the infusion tubing through the drip chamber of an infusion set by using a hydrophilic membrane which also eliminates the possibility of air trapping. The hydrophilic membrane has a defined wetting time and a defined mean pore size that will provide a defined bubble pressure point under gravitational pull to permit continuous air free infusion liquid flow there-through. The invention further provides an intravenous infusion set, wherein air bubbles cannot be sucked into the infusion line due to any deformation of the drip chamber caused by priming, or through the hydrophilic membrane due to the adjustment of the roller clamp along the infusion tubing, thereby ensuring safe replacement of the infusion bottle during multiple infusion procedures, thus preventing the occurrence of air embolism in patients, especially when the drip chamber is empty.

These and other aspects of the present invention will be better understood in the description below.

SUMMARY AND OBJECTS OF THE INVENTION

A primary object and advantage of the present invention is to provide an improved intravenous infusion set to administer continuous air free delivery of intravenous fluid to patients.

Another object and advantage of the present invention is to provide an improved intravenous infusion set to achieve auto-stop function once the drip chamber is empty.

Another object and advantage of the present invention is to provide an improved intravenous infusion set which is inexpensive to manufacture, efficient, effective and simple in its construction and use.

Another object and advantage of the present invention is to provide an improved intravenous infusion set which prevents the instances of air embolism.

Another object and advantage of the present invention is to provide an improved intravenous infusion set having a drip chamber with a flow regulating and stopping member which prevents the air from entering the flexible infusion line through the drip chamber as soon as it comes into contact with air.

Another object and advantage of the present invention is to provide an improved intravenous infusion set having a drip chamber with a flow regulating and stopping member which prevents infusion related infection.

Another object and advantage of the present invention is to provide an improved intravenous infusion set which prevents contaminants, microorganism, infectious agents or the like to enter the flexible infusion line.

Another object and advantage of the present invention is to provide an improved intravenous infusion set which helps reducing work load with respect to its installation and use, and ensures safe priming which may be crucial in critical conditions.

Another object and advantage of the present invention is to provide an improved intravenous infusion set, which can help in preparing a series of infusions at once, and which is quicker and more hygienic than ever before.

The flow regulating and stopping member is a hydrophilic membrane, which is permeable to fluid and impermeable to air. Preferably the material of hydrophilic membrane can be flexible and can be sheet or film, tube or fiber, or plug form. The material can be a fabric, such as a nonwoven, woven, or knit fabric, or a scrim.

The material can be made of paper such as filter paper, or a cloth, or a metal mesh. It can also be made of fiberglass, cellulosic, ceramic or the like. The material can also be a porous polymeric film or membrane, synthetic or natural, where the pores form the interstices or passageways. Representative polymers useful in the material include polyamide, nylon, polyurethane, polyester, polycarbonate, polyvinylidene fluoride, polyacrylic, polyolefins such as polyethylene and polypropylene, polytetrafluoroethylene, polyvinyl chloride and the like.

Accordingly, the present invention relates to an intravenous infusion set to administer continuous air free delivery of intravenous fluid to a patient, said intravenous infusion set comprising: a drip chamber, a flexible infusion line of sufficient length connecting a lower end of the drip chamber to a standard connector at the patient end so that a needle or a catheter could be connected to the patient; a roller clamp arranged between the drip chamber and the standard connector being movable along the length of the flexible infusion line, said drip chamber has a spike on the upper end and an infusion fluid outlet at the lower end of the drip chamber, said infusion fluid outlet is covered with a flow regulating and stopping member configured to administer continuous air free delivery of intravenous fluid to patients. The upper end of the drip chamber is also provided with an air closure cap together with a filter.

Said flow regulating and stopping member is a hydrophilic membrane which is sealed over the infusion fluid outlet at the lower end of the drip chamber. The hydrophilic membrane is effective when wet. The hydrophilic membrane is arranged in the drip chamber in a close fit manner eliminating the possibility of air being trapped or air bubbles being sucked into the infusion line. The hydrophilic membrane has a proximal face and a distal face. The proximal face of the hydrophilic membrane includes a sealing area which is used for sealing the membrane. The sealed hydrophilic membrane covers the outlet so that air bubbles and contaminants are prevented from entering the body of the patient during an infusion therapy.

The lower end of the lower chamber can end in a connector resulting into an outlet. The outlet can be connected to a flexible infusion line. The distal end of the connector can be sealed with the drip chamber. The hydrophilic membrane can cover the outlet so that air bubbles and contaminants are prevented from entering the body of the patient during an infusion therapy.

In one embodiment, the flow regulating and stopping member, i.e. the hydrophilic membrane, can be sealed on the proximal face of the disc. Alternatively, the flow regulating and stopping member, i.e. the hydrophilic membrane, can be sealed on the distal face of the disc. Further alternatively, the hydrophilic membrane can be sealed on both the proximal face and distal face of the disc.

The present invention embodies that the structure of the drip chamber can comprise shapes and configurations such as square, oval, rectangular, triangular, combinations thereof or the like etc. either wholly or partly along the length of the drip chamber.

The present invention embodies that the structure of the flow regulating and stopping member, which is permeable to fluid and impermeable to air, can comprise shapes and configurations such as square, oval, rectangular, triangular, combinations thereof or the like etc.

The drip chamber can normally be made of a suitable chemically inert plastic material. The present invention embodies that the drip chamber can also be made of other suitable materials such as ceramic, wood, metals and combinations thereof etc. Preferably, the wall of the drip chamber is transparent and flexible, being made of a flexible material. The wall of the drip chamber can also be rigid, being made of a rigid material.

The drip chamber can comprise a hollow lower chamber, which preferably is formed as a hollow cylinder, further preferably as a hollow circular cylinder, and further preferably having a uniform wall thickness. This ensures that the lower chamber, which forms a major part of the drip chamber, can be manufactured easily and cost efficiently, e.g. by extrusion.

The connector of the lower chamber can have a notch, which defines an inner wall and an outer wall of the connector, which walls are preferably parallel to each other. Preferably, the inner wall and the outer wall have respectively uniform wall thicknesses, are circular and extend coaxially to each other in order to define the notch in between. The notch, therefore, can be a circular gap in the connector, which gap is continuous in its longitudinal direction and which in a direction perpendicular to its longitudinal direction extends into the connector of the lower chamber, i.e. preferably in parallel to the walls of the lower chamber of the drip chamber. Hence, the notch can have a width which is preferably equal to or greater than the thickness of the wall of the lower chamber. Further, the wall of the lower chamber may be complementary to the notch of the connector, such that the wall of the lower chamber fits into the notch of the connector. Preferably, the wall of the lower chamber is sealed to at least one of the inner wall and/or the outer wall of the connector. Preferably, the inner wall is higher, i.e. extends further along the lower chamber, than the outer wall. Preferably, the wall of the lower chamber is sealed only to the inner wall.

The connector of the lower chamber can enclose one end of the lower chamber. Preferably, the connector is more rigid than the flexible lower chamber in a direction of force perpendicular to a main extension direction of the lower chamber.

The preferably flat and further preferably circular flow regulating and stopping member can be sealed on sealing leg or ring extending inside of the inner wall from the connector of the lower chamber and in parallel to one of the inner and/or outer wall. The sealing contact area of the flow regulating and stopping member with the sealing leg or ring can form a sealing area. Preferably, the sealing leg or ring is circularly arranged, while extending from the connector and being distanced from the inner wall and/or the wall of the lower chamber. Further preferably, the sealing leg or ring extends less than the inner wall and/or the outer wall from the connector along a main extension direction of the lower chamber. Preferably, the sealing area is arranged such that a remaining inner area and a remaining outer area of the flow regulating and stopping member, wherein the outer area is closest to the inner wall and/or the outer wall, have approximately the same size. The latter helps to ensure that liquid/fluid pressure inside the drip chamber results in equal forces on the inner area and the other area, thereby balancing the flow regulating and stopping member, so that it is less likely to bulge.

The above provisions ensure that applying a force to the drip chamber in a direction perpendicular to the main extension direction of the lower chamber will mainly only affect the flexible lower chamber. Thereby the connector of the lower chamber will maintain its shape and ensure that the exerted force is not transferred to the regulating and stopping member. In other words, the regulating and stopping member will remain tightly sealed to the connector.

The outlet can comprise a distal extension from the main body of the connector such that a fluid/liquid reservoir is formed on the distal side of the connector. Preferably, the sealing leg or ring forms the distal end of the reservoir opposite to a proximal reservoir bottom, wherein the distal extension protrudes distally from the reservoir bottom to define a ring-like reservoir around it.

Preferably, the distal extension extends within close proximity to the member and/or the sealing leg or ring, preferably more than 90%, more preferably more than 95%, of the distance between the reservoir bottom and the sealing leg or ring and/or the hydrophilic membrane.

Further preferably, the distal extension extends to the member and/or to the sealing leg or ring, such that they lie in the same plane perpendicular to the main extension direction of the drip chamber. Thereby, additional support for the member is provided which reduces the risk of failure.

Preferably, the distal extension of the outlet comprises one or more slits, preferably three slits, preferably periodically placed on the distal extension to connect the inside of the reservoir through the outlet with the outside in a direction perpendicular to the main extension direction of the drip chamber. Alternatively or in addition to the slits holes can be provided. Such slits and/or holes ensure that any errant air bubble that may have entered through the member/hydrophilic membrane is popped and does not exit the drip chamber.

The slits and/or holes may be located on a central portion which extends in a distal to proximal direction along the distal extension, preferably over more than 50% of the extension of the distal extension. At least some of the slits and/or holes may preferably extend from the reservoir bottom. Thereby, all fluid in the reservoir may pass through the outlet such that no fluid is left within the reservoir which may lead to infections.

Preferably, the slits are dimensioned such that air bubbles cannot enter. Preferably, the edge of the slits may be serrated/rough to improve a desired bubble burst.

The connector may be provided without the flow regulating and stopping member in order to be used with any medical device.

BRIEF DESCRIPTION OF THE ACCOMPANYING DRAWINGS

The foregoing and other objects, features, and advantages of the invention will be apparent from the following detailed description taken in conjunction with the accompanying drawings, wherein.

DETAILED DESCRIPTION OF THE INVENTION

Generally speaking, the term "proximal" refers to a region of the device or parts thereof or a location on the device which is closest to, for example, a user using the device. In contrast to this, the term "distal" refers to a region of the device which is farthest from the user, for example, the distal region of a needle will be the region of a needle containing the needle tip which is to be inserted e.g. into a patient's vein.

Figure 1:
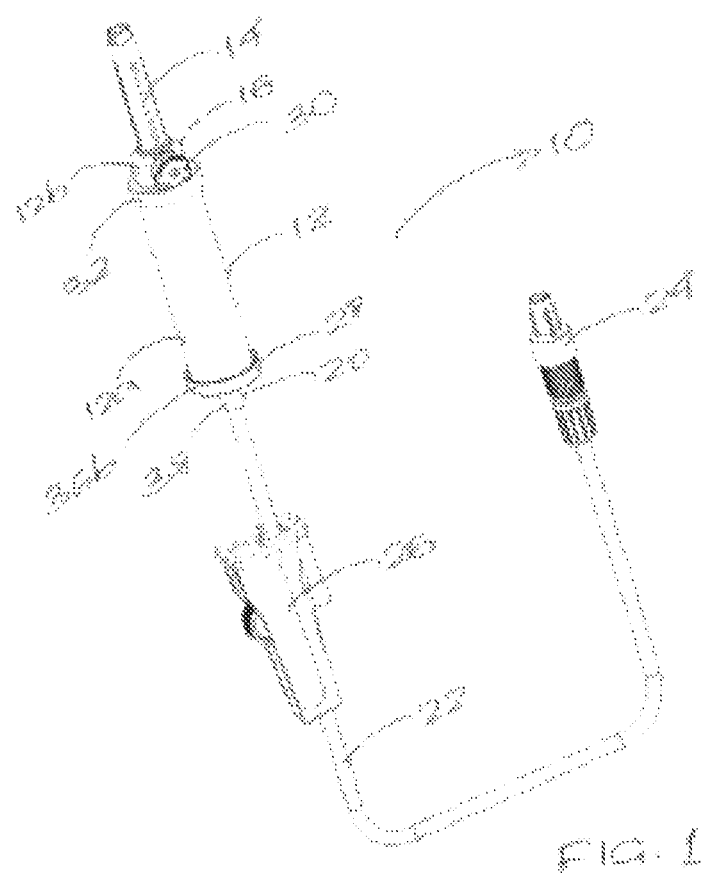
FIG. 1 is a schematic drawing of the intravenous infusion set of the present invention with an automatic fluid flow stopping mechanism provided in the drip chamber.

According to a first aspect of the present invention and referring to FIG. 1, one of the embodiments of an intravenous infusion set 10 is illustrated. The intravenous infusion set 10 comprises a drip chamber 12, said drip chamber 12 has a spike 14 on the upper end 16 and a flow regulating and stopping member 18 (see FIGS. 3 and 4) at its lower end. A flexible infusion line 22 of sufficient length connects a lower end 20 of a connector 28 of the drip chamber 12 to a standard connector 24 at the patient end so that a needle or a catheter could be connected to the patient. The connector 28 is funnel shaped.

A fluid flow adjustment device, such as a roller clamp 26, is arranged between the drip chamber 12 and the standard connector 24 being movable along the length of the flexible infusion line 22. The roller clamp 26 can be gradually adjusted so that the infusion line 22 could be squeezed proportionally to change the infusion rate and can also help in changing the fluid source, i.e. bottle or bag for multiple infusion procedures.

A clip (not shown) can also be arranged between the drip chamber 12 and the roller clamp 26 along the length of the flexible infusion line 22. The clip is configured to stop the flow of infusion fluid instantly by a clipping action. A Y-connector can also be provided between the drip chamber 12 and the standard connector 24.

Figure 2:
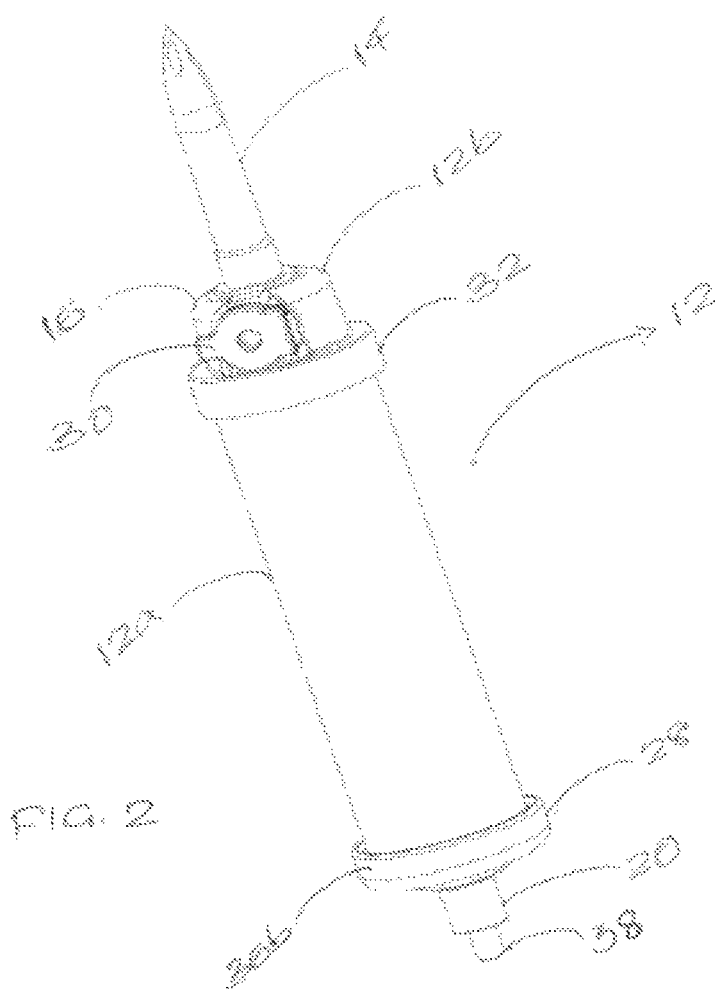
FIG. 2 is a side view of the drip chamber according to one embodiment of the present invention.
Figure 3:
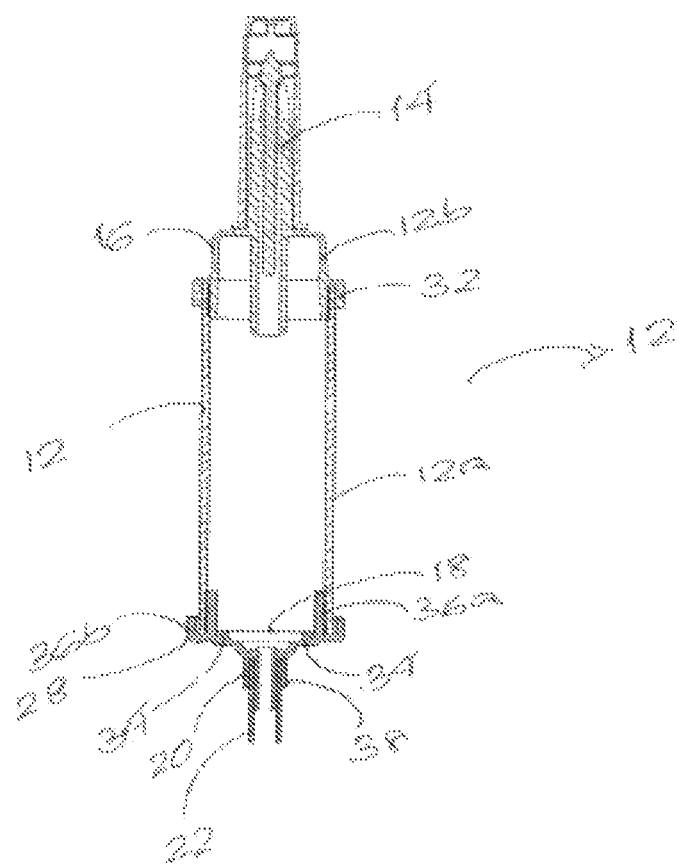
FIG. 3 is a cross-sectional view of the drip chamber according to one embodiment of the present invention.

As shown in FIGS. 1, 2 and 3, the drip chamber 12 is provided with at least two chambers comprising a lower chamber 12a, which is a hollow circular cylinder with a uniform wall thickness, and an upper chamber 12b. In this embodiment, the lower chamber 12a is flexible and the upper chamber 12b is rigid. Both of the chambers 12a, 12b are connected by a connecting means, such as a ring 32 defining a passage. The flexible lower chamber 12a is used for the purposes of priming. The upper end of the drip chamber 12 is also provided with an air closure cap 30 together with a filter.

In another embodiment, the lower chamber 12a is rigid and the upper chamber 12b is flexible. In yet another embodiment, both of the chambers 12a, 12b are flexible or rigid, or a combination thereof.

The drip chamber 12 is provided with a spike 14 on the upper end 16. The spike 14 has a pointed tip which is used to pierce a fluid bag/bottle (not shown) so that the infusion fluid will be pulled by gravity into the drip chamber 12. The spike 14 is provided with slits or holes for fluid to flow into the drip chamber 12 from the fluid bag/bottle to the patient.

Figure 4:
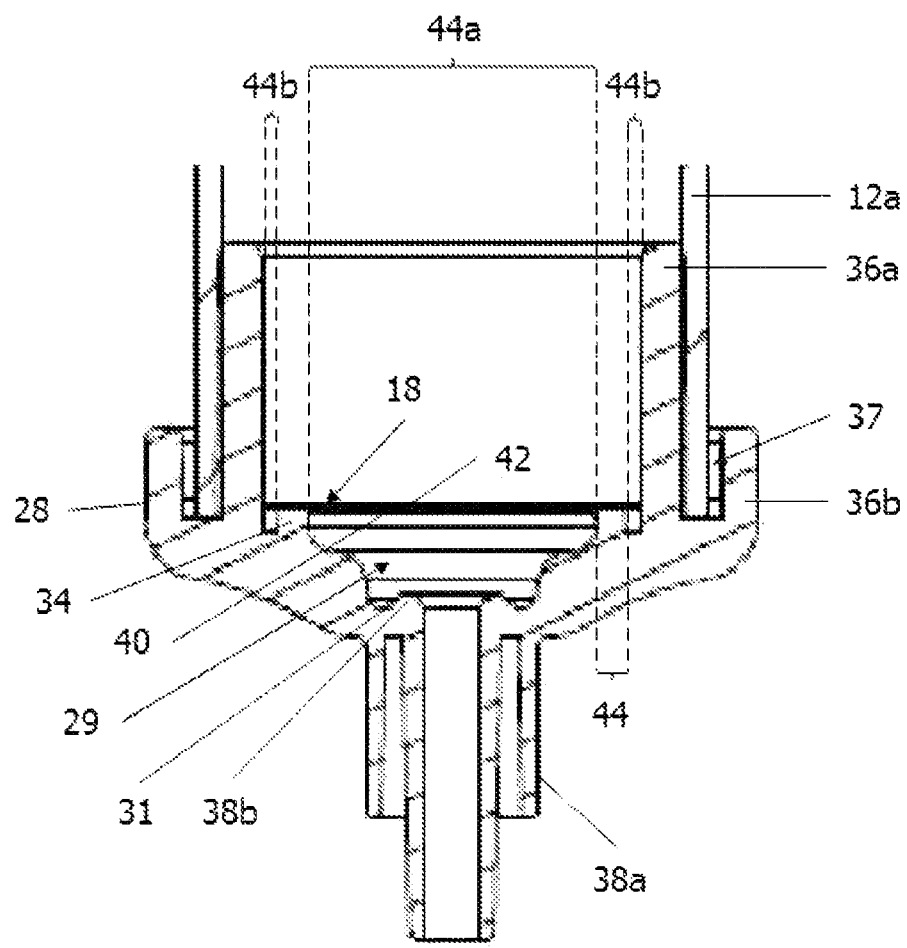
FIG. 4 is an enlargement of the lower part of the cross-sectional view of the drip chamber shown in FIG. 3 without the infusion line.

Referring now to FIGS. 2, 3 and 4, a lower end of the lower chamber 12a is sealed with the connector 28 resulting into an outlet 38. The outlet 38 comprises a proximal extension 38a and an opposite distal extension 38b from the main body of the connector 28, such that the proximal extension 38a is connected to the flexible infusion line 22 and the distal extension extends into a recessed reservoir 29 on the distal side of the connector 28. A flat and circular flow regulating and stopping member 18, which is a hydrophilic membrane, is sealed over said outlet 38. The connector 28 is provided with sealing leg or ring 34 with which the flow regulating and stopping member 18 is sealed. This sealing leg or ring 34 forms the distal end of the reservoir 29 opposite to a proximal reservoir bottom 31, wherein the distal extension 38b protrudes distally from the reservoir bottom 31 to define a ring-like reservoir 29 around it. The lower chamber 12a is sealed between an inner wall 36a and an outer wall 36b of the connector 28, wherein the inner wall 36a and the outer wall 36b form a circular notch 37 in between. The sealed hydrophilic membrane covers the outlet 38 so that air bubbles and contaminants are prevented from entering the body of the patient during an infusion therapy.

As illustrated in FIGS. 3 and 4, the flow regulating and stopping member 18, which is a hydrophilic membrane, is sealed over the sealing leg or ring 34 of the connector 28. The hydrophilic membrane is arranged to seat in the lower end of the lower chamber 12a in a close fit arrangement. No air passes when the flow regulating and stopping member 18 is wet. The flow regulating and stopping member 18 extends perpendicular to the main extension direction of the drip chamber 12, in particular of the lower chamber 12a, has a proximal face 40 and a distal face 42. The proximal face 40 of the member 18 includes a sealing area 44. The sealing area 44 of the member 18 is sealed onto said sealing leg or ring 34 and is arranged such that a remaining inner area 44a and a remaining outer area 44b of the flow regulating and stopping member, wherein the outer area is closest to the inner wall 36a, have approximately the same size. The sealed hydrophilic membrane 18 covers the outlet 38 so that air bubbles and contaminants are prevented from entering the body of the patient during an infusion therapy. The lower end of the lower chamber 12a ends in the connector 28 resulting into the outlet 38. The outlet 38 is connected to the flexible infusion line 22.

Alternatively, the flow regulating and stopping member 18, i.e. the hydrophilic membrane, can be sealed on the distal face 42. Further alternatively, the hydrophilic membrane 18 can be sealed on both the proximal face 40 and distal face 42.

The act of sealing referred above, for example sealing of flow regulating and stopping member 18 with the drip chamber 12, takes place by heat sealing, adhesive sealing, ultrasonic welding, heated die, radio frequency, mechanical seal, insert molding, laser welding, press/snap fit, annular ring with groove fitment, clamping, gluing or by the like processes etc.

The flow regulating and stopping member 18 which is a hydrophilic membrane of the present invention has a strong affinity for fluid/liquid while restricting air from attaching to its surface. As a result, the membrane is permeable to fluid/liquid and impermeable to air. A fully wetted hydrophilic membrane will allow fluid/liquid to flow through while acting like a barrier to air bubbles passing across it. Under normal conditions, flow of fluid/liquid from a fully wetted membrane is expected to start under gravity pull more readily. Hence with the present membrane setup, the fluid in the drip chamber will be ready to flow once it is filled up. No milking of the roller clamp is required to initiate the flow.

In the present invention, said hydrophilic membrane will automatically stop the fluid flow once the fluid in the drip chamber 12 is empty and as long as the membrane is still totally wet. As such, no air will get into the flexible infusion line 22 during and at the end of the infusion procedure. Furthermore, because the same intravenous infusion set 10 can be used for multiple infusions, the material cost and clinical waste is greatly reduced. This is one of the advantages of the present invention.

Figure 5:
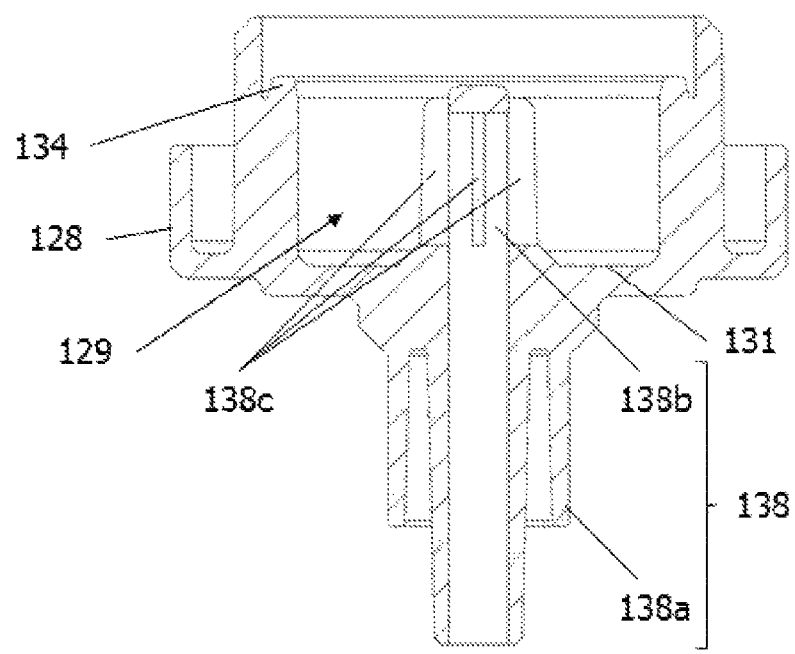
FIG. 5 is a cross-sectional view of a connector according to a further embodiment of the present invention.

Referring now to FIG. 5, a further embodiment is shown. In this embodiment an alternative connector 128 to the above drip chamber 12 is provided. Similar features are denoted with similar reference signs. This connector 128 also comprises on its distal side a recessed inner reservoir 129 with a reservoir bottom 131.

The difference in regard to the previous embodiment is that the distal extension 138b of the outlet 138 extends over a majority of the distance, preferably more than 50% of the distance, between the reservoir bottom 131 and the sealing leg or ring 134 and/or the member (not shown). Preferably, the distal extension 138b extends within close proximity to the member and/or the sealing leg or ring 134, i.e. more than 90%, more preferably more than 95%, of the distance between the reservoir bottom 131 and the sealing leg or ring 134 and/or the hydrophilic membrane. Further, the distal extension 138b extends to the member and/or to the sealing leg or ring 134, such that they lie in the same plane perpendicular to the main extension direction of the drip chamber 12. Preferably, the distal extension 138b of the outlet 138 comprises one or more slits 138c, e.g. three slits, preferably periodically placed on the distal extension to connect the inside of the reservoir 129 with the proximal extension 138a of the outlet 138 in a direction perpendicular to the main extension direction of the drip chamber 12. Alternatively or in addition to the slits 138c holes/perforations/openings (not shown) can be provided. Such slits and/or holes/perforations/openings, also referred to as a bubble bursting mechanism, ensure that any errant air bubble that may have entered through the member/hydrophilic membrane is popped and does not exit the drip chamber 12. The bubbles do not pass and burst before entering the infusion line 22. At the most only few or miniscule bubbles pass that have no or inconsequential impact on the patient or function of the device.

While in the present embodiment the slits 138c are located along a central portion which extends in a distal to proximal direction along the distal extension 138b, preferably over more than 50% of the extension of the distal extension 138b, they may preferably extend from the reservoir bottom 131. Thereby, all fluid in the reservoir 129 may pass through the outlet 138 such that no fluid is left within the reservoir 129 which may lead to infections. Thus, there is no stagnation of the fluids at the reservoir bottom 131.

Preferably, the slits 138c are dimensioned such that air bubbles cannot enter. Preferably, the edge of the slits may be serrated/rough to improve a desired bubble burst as part of a further improved bubble bursting mechanism.

In a further embodiment, the previous connector 128 is provided without the member/hydrophilic membrane 18 in order to be used with any medical device.

In a further embodiment, the previous connector 128 is provided with any kind of membrane 18 in order to be used with any medical device.

In a further embodiment, the reservoir 129 is manufactured integrally with the drip chamber 12.

In a still further embodiment, the drip chamber 12 and its components are unitarily constructed and manufactured.

In yet another embodiment, the drip chamber 12 and its components are constructed and manufactured separately and assembled as one device.

In yet another embodiment, the base portion of the drip chamber 12 can be made into two parts with the bubble bursting mechanism.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the scope of the invention as set forth in the claims.

Accordingly, it is not intended that the scope of the foregoing description be limited to the exact description set forth above, but rather that such description be construed as encompassing such features that reside in the present invention, including all the features and embodiments that would be treated as equivalents thereof by those skilled in the relevant art.

Thus, it is intended that the scope of the present invention herein disclosed should not be limited by the particular disclosed embodiments described above but should be determined only by a fair reading of the appended claims.

LIST OF REFERENCE NUMERALS 10 intravenous infusion set
12 drip chamber
12a lower chamber
12b upper chamber
14 spike
16 upper end
18 flow regulating and stopping member
20 lower end
22 infusion line
24 standard connector
26 roller clamp
28, 128 connector of the drip chamber
29, 129 reservoir
30 air closure cap
31, 131 reservoir bottom
32 ring
34, 134 sealing leg or ring
36a inner wall
36b outer wall
37 notch
38, 138 outlet
38a, 138a proximal extension of the outlet
38b, 138b distal extension of the outlet
40 proximal face
42 distal face
44 sealing area of the flow regulating and stopping member
44a inner area of the flow regulating and stopping member
44b outer area of the flow regulating and stopping member
138c slits

The invention claimed is:

1. An intravenous infusion set to administer continuous air free delivery of intravenous fluid to a patient, said intravenous infusion set comprising:
   a drip chamber comprising a lower end and an upper end, wherein the drip chamber is provided with a spike on the upper end and a flow regulating and stopping member at the lower end configured to administer continuous air free delivery of intravenous fluid to the patient;
   a flexible infusion line of a predetermined length connected to the lower end of the drip chamber; and
   wherein the lower end of the drip chamber comprises an inner wall and a sealing ring defining a sealing surface, the sealing ring being spaced from the inner wall so as to define a gap therebetween, the sealing ring defining an inner aperture, wherein the flow regulating and stopping member is seated within the drip chamber on the sealing surface of the sealing ring defining a sealing area, the flow regulating and stopping member covering the inner aperture of the sealing ring, the sealing surface of the sealing ring and the gap between the sealing ring and the inner wall, wherein an area of the flow regulating and stopping member extending over the inner aperture of the sealing ring defines a remaining inner area and an area of the flow regulating and stopping member extending over the gap between the sealing ring and the inner wall of the drip chamber defines a remaining outer area and where the remaining inner area and the remaining outer area have approximately the same size.

2. The intravenous infusion set as claimed in claim 1, wherein said flow regulating and stopping member is a hydrophilic membrane.

3. The intravenous infusion set as claimed in claim 1, wherein the drip chamber is provided with at least two chambers comprising a lower chamber and an upper chamber connected by a ring defining a passage.

4. The intravenous infusion set as claimed in claim 3, wherein a lower end of said lower chamber of the drip chamber is sealed with a connector resulting into an outlet which is connected to the flexible infusion line.

5. The intravenous infusion set as claimed in claim 1, wherein the flow regulating and stopping member has a proximal face and a distal face and the proximal face includes the sealing area.

6. The intravenous infusion set as claimed in claim 1, wherein said flow regulating and stopping member is sealed onto the sealing ring at said sealing area.

7. The intravenous infusion set as claimed in claim 2, wherein the hydrophilic membrane is sealable to the sealing ring by at least one of heat sealing, adhesive sealing, ultrasonic welding, heated die, radio frequency, mechanical seal, insert molding, laser welding, press and snap fit, and an annular ring with groove fitment.

8. The intravenous infusion set as claimed in claim 1, wherein said flow regulating and stopping member is sealed onto a distal face of the connector of the drip chamber.

9. The intravenous infusion set as claimed in claim 1, further comprising a roller clamp arranged between the drip chamber and a standard connector being movable along the length of the flexible infusion line.

10. The intravenous infusion set as claimed in claim 1, wherein the flexible infusion line is connected to an outlet that comprises a distal extension from a main body of a connector, wherein the distal extension comprises one or more slits having edges, wherein of the edges of the one or more slits are, at least one chosen from the group consisting of (i) serrated, and (ii) rough.

11. An intravenous infusion set to administer continuous air free delivery of intravenous fluid to a patient, said intravenous infusion set comprising:

a drip chamber comprising a lower end and an upper end, wherein the drip chamber is provided with a spike on the upper end and a flow regulating and stopping member at the lower end configured to administer continuous air free delivery of intravenous fluid to the patient;

a flexible infusion line of a predetermined length connecting to the lower end of the drip chamber; and a roller clamp arranged along the length of the flexible infusion line;

wherein the drip chamber is provided with at least two chambers comprising a lower chamber and an upper chamber connected by a connecting means comprising a ring defining a passage, wherein the lower end of said lower chamber is sealed with a connector resulting into an outlet which is connected to the flexible infusion line, and wherein the lower end of the drip chamber comprises an inner wall and a sealing ring defining a sealing surface, the sealing ring being spaced from the inner wall so as to define a gap therebetween, the sealing ring defining an inner aperture, wherein the flow regulating and stopping member is seated within the drip chamber on the sealing surface of the sealing ring defining a sealing area, the flow regulating and stopping member covering the inner aperture of the sealing ring, the sealing surface of the sealing ring and the gap between the sealing ring and the inner wall, wherein an area of the flow regulating and stopping member extending over the inner aperture of the sealing ring defines a remaining inner area and an area of the flow regulating and stopping member extending over the gap between the sealing ring and the inner wall of the drip chamber defines a remaining outer area and where the remaining inner area and the remaining outer area have approximately the same size.

12. The intravenous infusion set as claimed in claim 11, wherein the sealing ring is provided on the connector and forms a distal end of the fluid reservoir opposite to a proximal reservoir bottom, wherein the distal extension protrudes distally from the reservoir bottom to define a ring-like reservoir.

13. The intravenous infusion set as claimed in claim 11, wherein the outlet comprises a distal extension from a main body of the connector, such that a fluid reservoir is formed on a distal side of the connector, wherein the distal extension comprises one or more slits having edges, wherein the edges of the one or more slits are, at least one chosen from the group consisting of (i) serrated, and (ii) rough.

* * * * *